US008415371B2

(12) United States Patent
Halpern et al.

(10) Patent No.: US 8,415,371 B2
(45) Date of Patent: Apr. 9, 2013

(54) METHODS AND KITS FOR TREATING CLUSTER HEADACHE DISORDERS

(75) Inventors: John H. Halpern, Stow, MA (US); Torsten Harry Johannes Passie, Hannover (DE)

(73) Assignees: The McLean Hospital Corporation, Belmont, MA (US); Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 12/935,737

(22) PCT Filed: Sep. 4, 2009

(86) PCT No.: PCT/US2009/055971
§ 371 (c)(1),
(2), (4) Date: Dec. 14, 2010

(87) PCT Pub. No.: WO2010/033392
PCT Pub. Date: Mar. 25, 2010

(65) Prior Publication Data
US 2011/0104275 A1 May 5, 2011

Related U.S. Application Data

(60) Provisional application No. 61/097,773, filed on Sep. 17, 2008.

(51) Int. Cl.
*A01N 43/42* (2006.01)
(52) U.S. Cl.
USPC .............................. 514/279; 514/311; 514/563
(58) Field of Classification Search .................. 514/279, 514/311, 563
See application file for complete search history.

(56) References Cited

U.S. PATENT DOCUMENTS

| 3,228,959 A * | 1/1966 | Gyermek ....................... 548/504 |
| 4,524,072 A | 6/1985 | Zivin | |
| 4,808,588 A * | 2/1989 | King ........................ 514/213.01 |
| 2009/0264456 A1 | 10/2009 | Sewell | |

FOREIGN PATENT DOCUMENTS

WO WO 2004/112723 A2 12/2004

OTHER PUBLICATIONS

Sewell et al., Response of Cluster Headache to Psilocybin and LSD, 2006, Neurology, vol. 66, pp. 1920-1922.*
Balestrieri and Fontanari, "Acquired and Crossed Tolerance to Mescaline, LSD-25, and BOL-148," *Arch. Gen. Psychiatry* 1:279-282, 1959.
Friedman, "Headache. Pharmacological Approach to Treatment," *Calif. Med.* 95:145-149, 1961.
Frood, "Cluster Busters," *Nat. Med.* 13:10-11, 2007.
Halpern and Sewell, "Hallucinogenic Botanicals of America: A Growing Need for Focused Drug Education and Research," *Life Sci.* 78:519-526, 2005.

Halpern, "Hallucinogens and Dissociative Agents Naturally Growing in the United States," *Pharmacol. Ther.* 102:131-138, 2004.
Harvey et al., "Effects of d-Lysergic Acid Diethylamide, d-2-Bromolysergic Acid Diethylamide, dl-2,5-Dimethoxy-4-Methylamphetamine and d-Amphetamine on Classical Conditioning of the Rabbit Nictitating Membrane Response," *J. Pharmacol. Exp. Ther.* 221:289-294, 1982.
Karst et al., "The Non-Hallucinogen 2-Bromo-Lysergic Acid Diethylamide as Preventative Treatment for Cluster Headache: An Open, Non-Randomized Case Series," *Cephalalgia* 30:1140-1144, 2010.
Kimball et al., "Effect of Serotonin in Migraine Patients," *Neurology* 10:107-111, 1960.
Miller, "Isolation and Identification of Lysergic Acid Amide and Isolysergic Acid Amide as the Principal Ergoline Alkaloids in *Argyreia nervosa*, a Tropical Wood Rose," *J. A.O.A.C.* 53:123-127, 1970.
Rothlin, "Lysergic Acid Diethylamide and Related Substances," *Ann. NY Acad. Sci.* 66:668-676, 1957.
Schneckloth et al., "Effects of Serotonin Antagonists in Normal Subjects and Patients with Carcinoid Tumors," *Circulation* 16:523-532, 1957.
Sewell et al., "Response of Cluster Headache to Psilocybin and LSD," *Neurology* 66:1920-1922, 2006.
Sicuteri et al., "Treatment Specificity of Hallucinogenic and Non-Hallucinogenic Derivatives in Vascular Headaches," Excerpt from the "*Records from the international workings on selective psychostimulant drugs*" Rome, Jan. 25-26, 1963 (English translation submitted).
Sicuteri, "Hypothesis: Migraine, a Central Biochemical Dysnociception," *Headache* 16:145-159, 1976.
Sicuteri, "Mast Cells and Their Active Substances: Their Role in the Pathogenesis of Migraine," *Headache* 3:86-92, 1963.
Sicuteri, "Prophylactic Treatment of Migraine by Means of Lysergic Acid Derivatives," *Triangle* 67:116-125, 1963 (English translation submitted).
International Search Report for International Application No. PCT/US2009/055971, mailed Apr. 19, 2010.
Beck et al., "Management of Cluster Headache," *Am. Fam. Physician* 71:717-724, 2005.
Bertino et al., "Cholinesterase, d-Lysergic Acid Diethylamide, and 2-Bromolysergic Acid Diethylamide," *J. Clin. Exp. Psychopathol. Q. Rev. Psychiatry Neurol.* 20:218-222, 1959.
Dave et al., "The Time-Course for Up- and Down-Regulation of the Cortical 5-Hydroxytryptamine (5-HT)$_2$A Receptor Density Predicts 5-HT$_2$A Receptor-Mediated Behavior in the Rabbit," *J. Pharmacol. Exp. Ther.* 323:327-335, 2007.
Ekbom, "Prophylactic Treatment of Cluster Headache with a New Serotonin Antagonist, BC 105," *Acta. Neurol. Scand.* 45:601-610, 1969.
Friedman and Elkind, "Appraisal of Methysergide in Treatment of Vascular Headaches of Migraine Type," *JAMA* 184:125-128, 1963.
Ginzel and Mayer-Gross, "Prevention of Psychological Effects of d-Lysergic Acid Diethylamide (LSD 25) by Its 2-Brom Derivative (BOL 148)," *Nature* 178:210, 1956.
Graham, "Methysergide for Prevention of Headache; Experience in Five Hundred Patients over Three Years," *N. Engl. J. Med.* 270:67-72, 1964.
Gyermek, "5-Hydroxytryptamine Antagonists," *Pharmacol. Rev.* 13:399-439, 1961.

(Continued)

*Primary Examiner* — Ali Soroush
(74) *Attorney, Agent, or Firm* — Clark & Elbing LLP

(57) ABSTRACT

The invention features methods and kits employing bromolysergide in therapies for the treatment of cluster headache disorders.

20 Claims, 1 Drawing Sheet

OTHER PUBLICATIONS

Lovshin, "Use of Methysergide in the Treatment of Extracranial Vascular Headache," *Headache* 3:107-111, 1963.

Communication enclosing Extended European Search Report for European Patent Application No. 09814995.8, dated Mar. 23, 2012.

Office Action for Chinese Application No. 200980136477.X, dated Oct. 10, 2012 (6 pages).

* cited by examiner

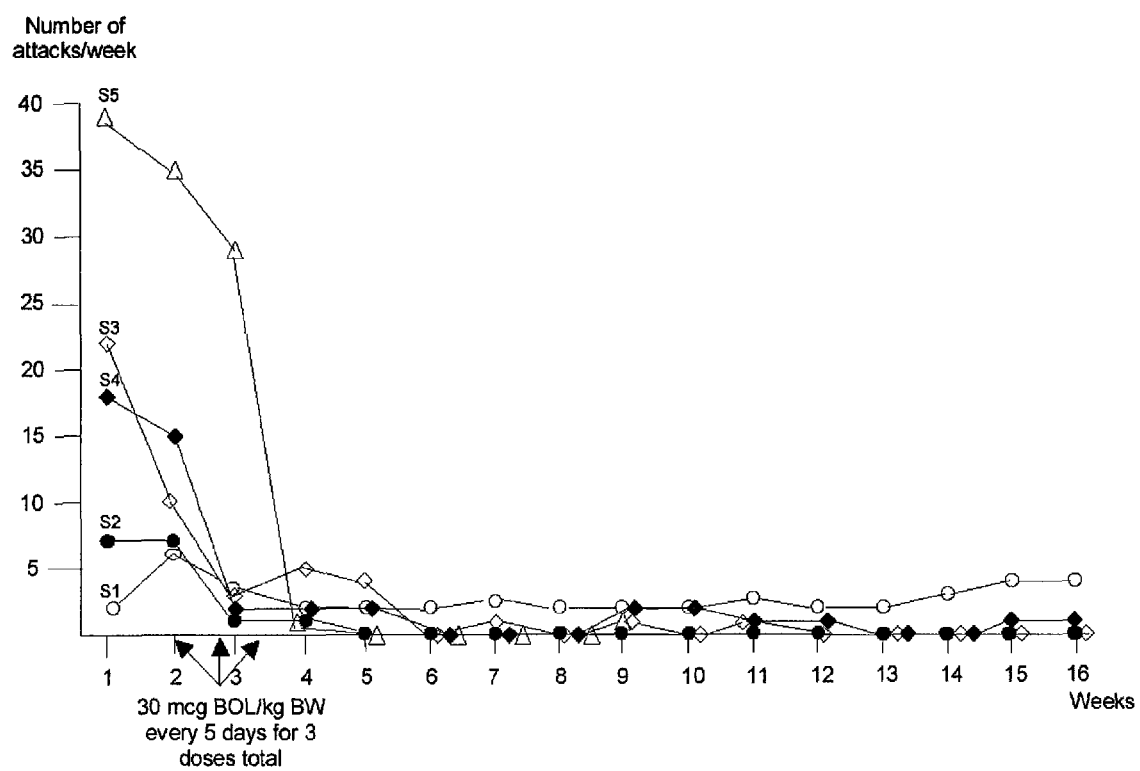

METHODS AND KITS FOR TREATING CLUSTER HEADACHE DISORDERS

CROSS REFERENCE TO RELATED APPLICATIONS

This application is a U.S. National Stage Application of International Patent Application No. PCT/US2009/055971, filed Sep. 4, 2009, which claims priority to U.S. Provisional Application No. 61/097,773, filed on Sep. 17, 2008, each of which is herein incorporated by reference in its entirety.

Statement Under 35 U.S.C. §103(c)(2)(C)

The claimed invention was made as a result of activities undertaken within the scope of a joint research agreement between John H. Halpern and Torsten Harry Johannes Passie.

BACKGROUND OF THE INVENTION

In general, the invention relates to therapies for cluster headache disorders.

Also known as "suicide headaches," cluster headaches are characterized by an extreme level of pain. Cluster headache disorders often manifest as recurring bouts of frequent attacks, called cluster periods, which may last from weeks to months. In episodic cluster headache disorder, cluster periods are interrupted by periods of remission when the attacks stop completely. In chronic cluster headache disorder, attacks continue unremittingly or with infrequent or brief remission periods.

Cluster headache disorders are not per se life-threatening; however, they are traumatic and debilitating. Although treatments exist, including abortive treatments (e.g., oxygen and sumatriptan) for stopping an initiated cluster headache attack and suppressive treatments (e.g., corticosteroids and lithium) for decreasing the frequency or severity of attacks, in some subjects, usually those with the chronic form, the disorder is medically intractable, with patients responding poorly or not at all to treatment. Thus, there remains a need for effective therapies for cluster headache disorders, particularly for chronic cluster headache disorder.

SUMMARY OF THE INVENTION

The invention features methods and kits for treating a recurrent cluster headache disorder in a subject and for extending the period of remission in a subject with a cluster headache disorder by administering bromolysergide.

In a first aspect, the invention features a method of treating a recurrent cluster headache disorder in a subject in need thereof by administering 2-bromolysergic acid diethylamide, or a pharmaceutically acceptable salt thereof, to the subject in an amount sufficient to treat the recurrent cluster headache disorder.

The invention also features a method of treating a chronic cluster headache disorder in a subject in need thereof by administering 2-bromolysergic acid diethylamide, or a pharmaceutically acceptable salt thereof, to the subject in an amount sufficient to treat the chronic cluster headache disorder.

The invention further features a method of treating an episodic cluster headache disorder in a subject in need thereof by administering 2-bromolysergic acid diethylamide, or a pharmaceutically acceptable salt thereof, to the subject in an amount sufficient to treat the episodic cluster headache disorder.

In a related aspect the invention features a method of extending the remission period of a subject with a cluster headache disorder, the method including administering 2-bromolysergic acid diethylamide, or a pharmaceutically acceptable salt thereof, to the subject while the subject is in remission in an amount sufficient to extend the remission period. In certain embodiments, the cluster headache disorder is episodic cluster headache disorder. In other embodiments, the cluster headache disorder is chronic cluster headache disorder. In particular embodiments, the subject is in remission, but is experiencing autonomic symptoms characteristic of an impending cluster headache attack.

In any of the above methods, the 2-bromolysergic acid diethylamide can be administered orally, subcutaneously, intravenously, or intramuscularly.

In any of the above methods, the method can include administering to the subject a dose of from 20 to 50 μg/kg of 2-bromolysergic acid diethylamide, two doses of from 20 to 50 μg/kg of 2-bromolysergic acid diethylamide administered over a period of 2 to 7 days, or three doses of from 20 to 50 μg/kg of 2-bromolysergic acid diethylamide administered over a period of 4 to 20 days.

In certain embodiments of the above methods, the method can include administering to the subject a unit dosage form including from 1.5 to 5 mg of 2-bromolysergic acid diethylamide. For example, the unit dosage form can include from 1.5 to 3.5 mg, 1.5 to 2.5 mg, 2.0 to 4.5 mg, 2.5 to 4.5 mg, 2.0 to 3.5 mg, 2.5 to 3.5 mg, 3.0 to 5.0 mg, 3.0 to 4.5 mg, 2.0 to 5.0 mg, or 2.0 to 4.0 mg of 2-bromolysergic acid diethylamide. In particular embodiments, two doses of the unit dosage form are administered to the subject over a period of 2 to 7 days. In still other embodiments, three doses of the unit dosage form are administered to the subject over a period of 4 to 20 days. For example, three doses of a unit dosage form including from 1.5 to 3 mg of 2-bromolysergic acid diethylamide can be administered to the subject over a period of 7 to 12 days. In one particular embodiment, three doses of a unit dosage form including from 1.5 to 3 mg of 2-bromolysergic acid diethylamide is administered to the subject once every five days over a period of 11 days.

In a particular embodiment of any of the above methods, the subject has a cluster headache disorder that is refractory to one or more prophylactic therapies. For example, the cluster headache disorder can be refractory to treatment using corticosteroids (e.g., hydrocortisone, prednisone, methylprednisolone, triamcinolone, bethamethasone, and dexamethasone, among other corticosteroids); tricyclic antidepressants (e.g., amitriptyline, amoxapine, clomipramine, desipramine, dothiepin, doxepin, imipramine, lofepramine, maprotiline, mianserin, mirtazapine, nortriptyline, octriptyline, oxaprotiline, protriptyline, and trimipramine, among other tricyclic antidepressants); calcium channel blockers (nifedipine, amlodipine, felodipine, flunarizine, isradipine, nicardipine, diltiazem, verapamil, and bepridil, among other calcium channel blockers); beta blockers (e.g., propanolol, nadolol, timolol, pindolol, labetolol, metoprolol, atenolol, esmolol, acebutolol, carvedilol, bopindolol, carteolol, oxprenolol, penbutolol, medroxalol, bucindolol, levobutolol, metipranolol, bisoprolol, nebivolol, betaxolol, celiprolol, solralol, and propafenone, among other beta blockers); anticonvulsants (e.g., valproate and topiramate, among other anticonvulsants); methysergide; and/or lithium.

In a related aspect, the invention features a kit including: (i) a pharmaceutical composition including 2-bromolysergic acid diethylamide, or a pharmaceutically acceptable salt thereof; and (ii) instructions for administering the composition to a subject for the treatment of a recurrent cluster headache disorder.

The invention further features a kit including: (i) a pharmaceutical composition including 2-bromolysergic acid diethylamide, or a pharmaceutically acceptable salt thereof; and (ii) instructions for administering the composition to a subject for the treatment of chronic cluster headache disorder.

The invention also features a kit including: (i) a pharmaceutical composition including 2-bromolysergic acid diethylamide, or a pharmaceutically acceptable salt thereof; and (ii) instructions for administering the composition to a subject for the treatment of episodic cluster headache disorder.

The invention further features a kit including: (i) a pharmaceutical composition including 2-bromolysergic acid diethylamide, or a pharmaceutically acceptable salt thereof; and (ii) instructions for administering the composition to a subject for extending the remission period of a subject with a cluster headache disorder. In certain embodiments, the cluster headache disorder is episodic cluster headache disorder or chronic cluster headache disorder.

In certain embodiments of the above kits, the pharmaceutical composition is a unit dosage form (e.g., a tablet, capsule, or caplet) including 1.5 to 5 mg of 2-bromolysergic acid diethylamide, or a pharmaceutically acceptable salt thereof.

In a particular embodiment of the above kits, the kit of the invention includes from two to four doses (e.g., two, three, or four doses) of the pharmaceutical composition and instructions for administering the doses to the subject over a period of 4 to 20 days, or any other dosing regimen described herein.

As used herein, "bromolysergide" refers to the compound 2-bromolysergic acid diethylamide or a pharmaceutically acceptable salt of 2-bromolysergic acid diethylamide.

By a "cluster headache disorder" is meant a disorder characterized by frequent attacks of short lasting, severe, uniform, unilateral head pain associated with autonomic symptoms occurring ipsilateral to the pain (e.g. lacrimation and/or nasal congestion) (see, for example, Headache Classification Committee of the International Headache Society (2004) The International Classification of Headache Disorders, 2nd edn. Cephalalgia 24 Suppl 1: 1-160). The pain is generally intense and is often described as a burning, boring, stabbing or piercing sensation. For example, a subject with a cluster headache disorder can have at least 2, 3, 4, or 5 attacks of severe unilateral orbital, supraorbital, and/or temporal pain lasting 15-180 minutes each and having an average frequency of from one every other day to 8 per day if left untreated. The attacks, referred to herein as "cluster headache attacks" or simply "attacks," are associated with one or more of the following autonomic symptoms occurring ipsilateral to the pain: conjunctival injection and/or lacrimation; nasal congestion and/or rhinorrhoea; eyelid edema; forehead and facial sweating; and miosis and/or ptosis. The attacks may also be associated with a sense of restlessness or agitation. During part (but less than half) of the time-course of a cluster period, attacks may be less severe and/or of shorter or longer duration. During part (but less than half) of the time-course of a cluster period, attacks may be less frequent. Attacks usually occur in series (cluster periods) lasting for weeks or months separated by remission periods usually lasting weeks, months, or years. During a cluster period, attacks occur regularly and may be provoked by alcohol, histamine, or nitroglycerin. Pain is maximal orbitally, supraorbitally, temporally, or in any combination of these sites, but may spread to other regions of the head. Pain almost invariably recurs on the same side during an individual cluster period. During the worst attacks, the intensity of pain is excruciating. Patients are usually unable to lie down and characteristically pace the floor. Cluster headache disorders include, but are not limited to, cluster headache with coexistent trigeminal neuralgia (cluster-tic syndrome), episodic cluster headache disorder, and chronic cluster headache disorder. Cluster headache is typically diagnosed by a well characterized clinical presentation.

By "episodic cluster headache disorder" is meant a disorder in which the subject meets the criteria for cluster headache disorder and experiences at least two cluster periods lasting 7 to 365 days cumulative separated by pain-free remission periods of about one month or longer. For example, a subject with episodic cluster headache disorder may experience an attack once every other day for a period of three weeks, followed by a remission period lasting two months before the occurrence of another cluster period. Subjects with episodic cluster headache disorder typically have cluster periods lasting between 2 weeks and 3 months.

By "chronic cluster headache disorder" is meant a disorder in which the subject meets the criteria for cluster headache disorder and experiences attacks unremittingly or with infrequent or short remission periods of less than about one month cumulative over a period of a year. For example, a subject with chronic cluster headache disorder may experience an attack once every other day for a period of 200 days, followed by a pain free remission period of 15 days, followed by one or more attacks daily for 150 days. Chronic cluster headache disorder may arise de novo or evolve from the episodic cluster headache disorder.

By a "recurrent cluster headache disorder" is meant chronic cluster headache disorder or episodic cluster headache disorder.

By "remission period" is meant a period of at least two days during which a subject with a cluster headache disorder does not experience any cluster headache attacks. The remission period may be, e.g., 2, 10, 30, or 90 days, or 1, 2, or 10 years.

By "extending the remission period" is meant delaying the occurrence of a cluster period in a subject with a cluster headache disorder who is in remission and undergoing a therapy of the invention relative to the length of remission period that would have been experienced by the subject in the absence of treatment, or relative to the average length of remission experienced by a matched set of subjects with a cluster headache disorder of similar type and severity who are not undergoing a therapy of the invention. The delay extending the remission period may be, e.g., at least 2, 7, 30, 90, or 180 days. Thus, in the claims and embodiments, "extending the remission period" involves the administration to a subject who is already in remission for prophylactic purposes.

As used herein, the term "autonomic symptoms" refers to a change in an autonomic function in a subject. Examples of autonomic symptoms include, but are not limited to, postural hypotension, increased forehead and facial sweating, dry eyes, dry mouth, and failure of accommodation (e.g., dilated pupils or miosis), ptosis, lacrimation, eyelid edema, and/or rhinorrhea.

As used herein, "treating" refers to administering a pharmaceutical composition for therapeutic purposes. "Therapeutic treatment" refers to providing treatment to a subject suffering from a disorder to ameliorate the disorder and improve the subject's condition. Thus, in the claims and embodiments, treating a subject with a cluster headache disorder involves the administration of a composition to the subject for therapeutic purposes.

The term "administration" or "administering" refers to a method of giving a dose of a pharmaceutical composition to a patient, where the method is, e.g., oral, topical, subcutaneous, by inhalation, intravenous, intraperitoneal, intracerebroventricular, intrathecal, or intramuscular. The preferred method of administration can vary depending on, e.g., the components of the pharmaceutical composition, the general health of the patient, and the severity of the disorder.

As used herein, the terms "an amount sufficient" and "sufficient amount" refer to the amount of bromolysergide required to achieve therapeutic effects in a subject diagnosed with a cluster headache disorder. Therapeutic effects can include, but are not limited to, (i) diminution of pain during a cluster period, (ii) inducing early remission from cluster period, (iii) decreasing the frequency of acute attacks during a cluster period, (iv) converting a chronic cluster headache disorder to an episodic cluster headache disorder, (v) extending the remission period of a subject between cluster periods, (vi) reducing the severity of one or more non-pain symptoms associated with an attack (i.e., ipsilateral conjunctival injection and/or lacrimation; ipsilateral nasal congestion and/or rhinorrhoea; ipsilateral eyelid edema; ipsilateral forehead and facial sweating; ipsilateral miosis and/or ptosis; and a sense of restlessness or agitation), or (vii) reducing sensitivity to agents, such as alcohol, histamine, and nitroglycerin, which can provoke a cluster headache attack. The amount sufficient used to practice the invention for therapeutic treatment of conditions caused by, or contributed to by, a cluster headache disorder can vary depending upon the manner of administration, the age, body weight, and general health of the subject. Ultimately, the attending physician will decide the appropriate amount and dosage regimen. Such amount is referred to as an "amount sufficient."

Other features and advantages of the invention will be apparent from the Drawings, Detailed Description, and the claims.

BRIEF DESCRIPTION OF THE DRAWINGS

FIG. 1 is a graph depicting the change in the number of cluster attacks experienced by five subjects following, and just prior to, bromolysergide administration (3×30 µg/kg; see Example 3). For these five treatment-refractory cluster headache patients, the results show that three single doses of bromolysergide over a 10 day period can either break a cluster headache cycle or considerably improve the frequency and intensity of attacks, even resulting in changing from a chronic state to an episodic form with remission extending for months.

DETAILED DESCRIPTION

The invention features methods and kits for treating a recurrent cluster headache disorder in a subject and for extending the period of remission in a subject with a cluster headache disorder by administering bromolysergide.

Bromolysergide

Also known as bromo-LSD, BOL, BOL 148, (8β)-2-bromo-9,10-didehydro-N,N-diethyl-6-methylergoline-8-carboxamide, 2-bromo-N,N-diethyl D-lysergamide, and bromolysergide, the compound 2-bromolysergic acid diethylamide has the following structure:

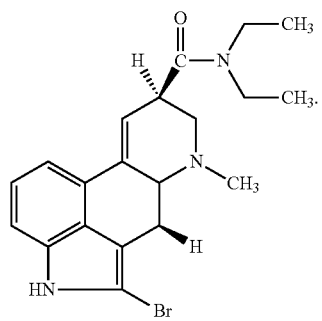

The synthesis of 2-bromolysergic acid diethylamide has been described by Troxler and Hofmann (Helv. Chim. Acta 40:2160 (1957)).

Pharmaceutically acceptable salts of 2-bromolysergic acid diethylamide can also be useful in the methods and kits of the invention. Salts that can be used in the preparation of bromolysergide include non-toxic acid addition salts or metal complexes that are commonly used in the pharmaceutical industry. Examples of acid addition salts include organic acids, e.g., acetic, lactic, pamoic, maleic, citric, malic, ascorbic, succinic, benzoic, palmitic, suberic, salicylic, tartaric, methanesulfonic, toluenesulfonic, or trifluoroacetic acids; polymeric acids, e.g., tannic acid or carboxymethyl cellulose; and inorganic acids, e.g., hydrochloric acid, hydrobromic acid, sulfuric acid, or phosphoric acid. Metal complexes include, e.g., calcium, zinc, and iron.

Formulations and Administration

Formulations of bromolysergide can include, but are not limited to, solutions, suspensions, tablets, or capsules. Methods well known in the art for making formulations are found, for example, in "Remington: The Science and Practice of Pharmacy" (21st ed.) ed. A. R. Gennaro, 2005, Lippincott, Philadelphia, Pa. The concentration of the compound in the formulation will vary depending upon a number of factors, including the volume to be administered and the route of administration. The dosage of drug to be administered is likely to depend on such variables as the severity of the disorder, the overall health status of the particular subject, the formulation of the compound, and its route of administration.

Effective dosage ranges for bromolysergide are generally between about 10 µg/kg and about 100 µg/kg body weight. Desirably, a dose of between about 20 µg/kg to about 50 µg/kg body weight is administered. For example, a dose of 2.4 mg may be administered to a 80 kg adult to deliver about 30 µg/kg bromolysergide. Bromolysergide can be administered to a subject by a route that is suitable for the formulation, e.g., by oral, subcutaneous, intravenous, or intramuscular administration. Several doses may be administered on different days (e.g., as described in the examples).

Therapy

Bromolysergide can be administered to treat a subject with a recurrent cluster headache disorder. The recurrent cluster headache disorder may be episodic or chronic. In this embodiment of the invention, the therapeutic effects of administration of bromolysergide can include diminution or elimination of the pain experienced by the subject during an attack, a decrease in frequency of attacks during the cluster period, or amelioration of other symptoms associated with cluster headache disorders. Applicants have discovered that bromolysergide need not be administered continually as the therapeutic effects of administration can persist for several weeks or several months following administration (see, for instance, Examples 1 and 3).

Bromolysergide can also be administered to a subject with a cluster headache disorder for the purpose of extending the period of remission. For example, the bromolysergide can be administered to extend the period of remission indefinitely (e.g., extend the period of remission more than 2 months, 4 months, or 1 year). In some instances, the bromolysergide is administered while the subject is experiencing autonomic symptoms characteristic of an impending cluster headache attack.

Kits

Bromolysergide can be packaged in a kit for carrying out the methods of the invention. The kit may be manufactured as a single use unit dose for one patient, multiple uses for a particular patient; or the kit may contain multiple doses suitable for administration to multiple patients ("bulk packaging"). The kit components may be assembled in cartons, blister packs, bottles, tubes, and the like. Kits may also include instructions for administering the pharmaceutical compositions using any indication and/or dosing regimen described herein.

The following examples are put forth so as to provide those of ordinary skill in the art with a complete disclosure and description of how the methods and kits claimed herein are used, and are intended to be purely exemplary of the invention and are not intended to limit the scope of what the inventors regard as their invention.

Example 1

Treatment of Chronic Cluster Headache Disorder with Bromolysergide

The desired amount of bromolysergide (hydrochloride salt) was mixed with dextrose and placed into gelatin capsules for administration to subjects suffering from chronic cluster headache disorder.

Bromolysergide was administered to two adult subjects diagnosed with chronic cluster headache disorder during a cluster period. A dose of 2 mg of 2-bromolysergic acid dethylamide (30 μg/kg body weight) was administered orally to subject 1 three times, once every five days. A dose of 2.5 mg of 2-bromolysergic acid dethylamide (approximately 30 μg/kg body weight) was administered orally to subject 2 three times, once every five days.

Subjects were asked to rate their symptoms following administration of bromolysergide.

Subject 1 rated the results as "minimally improved" (Clinical Global Impressions Scale), reporting a 30% reduction in pain and 30% reduction of attack frequency for ten weeks. After ten weeks, the cluster headache disorder of subject 1 reverted to its pre-treatment form.

Subject 2 rated the results as "marked/very much improved" (Clinical Global Impressions Scale), and reported complete or nearly complete remission of symptoms. The improvement in subject 2 was so substantial that the subject no longer met criteria set forth by the International Headache Society for initial diagnosis with chronic cluster headache disorder. Subject 2 remained free of attacks for more than 3 months (at last follow-up), despite having suffered from unremitting chronic cluster headache disorder for more than 6 years.

Example 2

Extending the Remission Period of a Cluster Headache Disorder

Bromolysergide can also be administered to subjects diagnosed with a cluster headache disorder to extend the remission period.

A subject who is diagnosed with episodic cluster headache disorder and is in remission is selected for treatment with bromolysergide. After 6 months of remission, the subject experiences an autonomic symptom characteristic of an impending cluster headache attack, e.g., miosis and/or rhinorrhea, and receives three doses of bromolysergide (3×1.5 mg administered orally), the first dose on the day the subject first experiences the autonomic symptoms (day 0), the second dose five days later (on day 5), and the third dose ten days following the appearance of the autonomic symptom. With therapeutic intervention, the impending cluster headache attack may be aborted and the remission period may last an additional 1, 2, 3, 4, 5, or 6 months.

A subject who is diagnosed with chronic cluster headache disorder and is in remission is selected for treatment with bromolysergide. After a cluster period lasting 20 months, the subject goes into remission. On day 3, day 8, and day 13 of the remission period, the subject receives 3 mg bromolysergide administered orally. With therapeutic intervention, the remission period may be extended for several weeks or several months.

As a result of the therapeutic intervention, both subjects can benefit from an extended remission period, i.e., an absence of cluster headache attacks for a period longer than the period would have been in the absence of therapeutic intervention.

Example 3

Treatment of Chronic Cluster Headache Disorder with Bromolysergide in Treatment-Refractory Cluster Headache Patients Patients referred to the Pain Clinic at the Hannover Medical School were identified with cluster headache if they met the respective diagnostic criteria of the international classification of headache disorders (Headache Classification Committee of the International Headache Society (2004) The International Classification of Headache Disorders, 2nd edn. Cephalalgia 24 Suppl 1:1-160). In addition, all patients were non-responders to verapamil and other prophylactic medications (i.e., refractory to the prophylactic medications listed in Table 1 for each patient). In accordance with German national and local ethics committee rules, all patients signed an informed consent, in which the patients declared their agreement to participate in this project on the compassionate use of bromolysergide for cluster headache. Patients kept a standardized daily diary of cluster headache symptoms starting at least two weeks prior to bromolysergide administration. Bromolysergide (hydrochloride salt) was manufactured by THCpharm GmbH (Frankfurt am Main, Germany). A purity of >99.2% was identified by HPLC and other analytical tests. Bromolysergide hydrochloride 30 μg per Kg body weight was dissolved into distilled water and then given once every 5 days for a total of 3 doses per os. Alterations in consciousness, thought disturbances, and vital signs (blood pressure, heart rate) were measured during a three to four hour observational period following administration. Patients were asked to continue completing daily headache diaries for the next months or until they experience 3 days of attacks of a starting new cluster series.

The results are summarized below in Table 1 and FIG. 1. One patient (S2) with episodic cluster headache and four patients with the chronic form participated. All but one patient (S1) had symptoms for more than 10 years. Patient S2 noted the termination of his cluster period and a long-lasting remission period of six months (at last follow-up) and continuing. Patients S3 and S5 reported a pronounced reduction of attack frequency, which included a continuous greater than 4-week period of attack quiescence indicating the transition from a chronic to an episodic form. Patient S4 did not show a continuous 4-week break of attacks but nevertheless did show a profound reduction of attack frequency. In addition, patients S3 and S4 showed such reductions of pain intensity during their remaining occasional attacks that they no longer administered an acute intervention as they had prior to receiving the bromolysergide treatment. Although patient S1 did not show this pronounced attack reduction similar to the other 4 patients, he indicated a decrease of attack intensity of about 30% within the first 4 months. It is likely relevant that patient S1 continued to drink alcohol (contrary to advice), a known and common trigger for attacks.

No changes to heart rate and blood pressure were observed during bromolysergide treatment. Most of the patients recorded some kind of "flabby" or "light drunk" feelings. Patient S2 noted a "funny" feeling, tense muscles, and sweating of his hands. These mild subjective effects lasted from one to two hours. No visual hallucinations or distortions occurred nor was there any evidence of delusional thinking or overt psychosis.

For the first five treatment-refractory cluster headache patients enrolled, the non-hallucinogen bromolysergide was quite effective at breaking cluster headache cycle and not just a single headache attack. The results show that three single doses of bromolysergide within 10 days can either break a cluster headache cycle or considerably improve the frequency and intensity of attacks, even resulting in changing from a chronic state to an episodic form with remission extending for many months or longer. Except for very mild alterations of subjective state and mild to no sympathetic reactions for about 2 hours, no other side effects were observed.

Interestingly, patient S4's cluster headache was refractory to methysergide, which the patient stopped taking in 1978. While bromolysergide is non-hallucinogenic, methysergide in supra-therapeutic doses is hallucinogenic (i.e., ca. 4 mg methysergide is estimated to be equivalent to 25 micgrograms LSD; see Abrahamson et al., J. Asthma Res. 3:81 (1965)). Methysergide is used for the prophylactic treatment of cluster headache disorders. It is typically administered daily and, over time, the longstanding user is at risk to develop the very serious medical complication of fibrotic reactions (retroperitoneal, pulmonary, pleural, and cardiac) although these are rare (see Kudrow L: Comparative results of prednisone, methysergide, and lithium therapy in cluster headache, in Greene R (ed): Current Concepts in Migraine Research. New York: Raven Press, pp. 159-163 (1978); Kudrow L. Cluster headache: mechanisms and management. New York: Oxford University Press, (1980); Zakrzewska J. M., Br J. Oral Maxillofac. Surg. 39:103 (2001); Curran et al., Res. Clin. Stud. Headache 1:74 (1967); Krabbe A., Cephalalgia 9:404 (1989); and Graham et al., N. Eng. J. Med. 274:359 (1966)).

The current standard of care involves interventions that break single headache attacks and reduce pain duration, frequency, and intensity of attack cycles, but without approved treatments that extend remission. In contrast, we have demonstrated that treatment with bromolysergide can break a cluster headache cycle, convert a chronic cluster headache disorder into an episodic cluster headache disorder, and extend the remission period of a subject suffering from a cluster headache disorder.

TABLE 1

Patient information and clinical aspects.

|  | Subject | | | | |
|---|---|---|---|---|---|
|  | S1 | S2 | S3 | S4 | S5 |
| Sex (m/f) | m | m | m | m | m |
| Age (years) | 46 | 28 | 47 | 41 | 41 |
| Body weight (kg) | 83 | 68 | 106 | 105 | 74 |
| Body height (cm) | 180 | 168 | 188 | 195 | 174 |
| Years of illness | 3 | 10 | 10 | 33 | 32 |
| Cranial side of attacks | left | right | right[a] | right | right |
| Cluster headache form | chronic | episodic | chronic since 2005 | chronic since 2001 | chronic since 2007 |
| Attacks per week[b] | 6 | 7 | 10 | 15 | 19 |
| Mean intensity of attacks (VAS)[b] | 8.4 | 8.3 | 5.5 | 6.4 | 7.0 |
| Treatments (acute) | sumatriptan i.n. | oxygen | Frovatriptan[c] oxygen | oxygen sumatriptan s.c. | oxygen |
| Treatments (prophylactic) | verapamil 240 mg/d | verapamil 240 mg/d | verapamil 240 mg/d | verapamil 320 mg/d[d] | verapamil 960 mg/d[e] |
| BOL (30 μg/kg)[f] | 2.5 mg | 2.0 mg | 3.1 mg | 3.1 mg | 2.2 mg |
| Side effects[g] | "flabby feeling" | "funny feeling" | "slightly tipsy" | "slightly tipsy" | "slightly tipsy" |
| Vital signs | unchanged | unchanged | unchanged | unchanged | unchanged |

[a]Left (from 1999-2005), right (since 2005).
[b]In the preassessment week.
[c]Up to TID 2.5 mg.
[d]Taken for 3 months. Also refractory to methysergide (taken for 1 year in 1978); prednisone (only for 5 days); and lithium for 3 months.
[e]Also prednisone (only for 4 days); lithium for 3 days; and doxepine (10 mg).
[f]Bromolysergide (BOL) administered three times within 10 days (e.g., on days 1, 5, and 10).
[g]Each of the subjects reported experiencing a side effect for about 2 hours.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating a recurrent cluster headache disorder in a subject in need thereof, said method comprising administering 2-bromolysergic acid diethylamide, or a pharmaceutically acceptable salt thereof, to said subject in an amount sufficient to treat said recurrent cluster headache disorder, wherein said subject has a recurrent cluster headache disorder that is refractory to one or more, prophylactic therapies.

2. A method of treating a chronic cluster headache disorder in a subject in need thereof, said method comprising administering 2-bromolysergic acid diethylamide, or a pharmaceutically acceptable salt thereof, to said subject in an amount sufficient to treat said chronic cluster headache disorder, wherein said subject has a chronic cluster headache disorder that is refractory to one or more prophylactic therapies.

3. A method of treating an episodic cluster headache disorder in a subject in need thereof, said method comprising administering 2-bromolysergic acid diethylamide, or a pharmaceutically acceptable salt thereof, to said subject in an amount sufficient to treat said episodic cluster headache disorder, wherein said subject has an episodic cluster headache disorder that is refractory to one or more prophylactic therapies.

4. A method of extending the remission period of a subject with a cluster headache disorder, said method comprising administering 2-bromolysergic acid diethylamide, or a pharmaceutically acceptable salt thereof, to said subject while said subject is in remission in an amount sufficient to extend said remission period, wherein said subject has a cluster headache disorder that is refractory to one or more prophylactic therapies.

5. The method of claim 4, wherein said cluster headache disorder is episodic cluster headache disorder.

6. The method of claim 4, wherein said cluster headache disorder is chronic cluster headache disorder.

7. The method of claim 4, wherein said subject is experiencing autonomic symptoms characteristic of an impending cluster headache attack.

8. The method of any one of claims 1-4, wherein a dose of from 20 to 50 µg/kg of 2-bromolysergic acid diethylamide, or a pharmaceutically acceptable salt thereof, is administered to said subject.

9. The method of claim 8, wherein two doses of from 20 to 50 µg/kg of 2-bromolysergic acid diethylamide, or a pharmaceutically acceptable salt thereof, are administered to said subject over a period of 2 to 7 days.

10. The method of claim 9, wherein three doses of from 20 to 50 µg/kg of 2-bromolysergic acid diethylamide, or a pharmaceutically acceptable salt thereof, are administered to said subject over a period of 4 to 20 days.

11. The method of any one of claims 1-4, wherein a unit dosage form comprising from 1.5 to 5 mg of 2-bromolysergic acid diethylamide, or a pharmaceutically acceptable salt thereof, is administered to said subject.

12. The method of claim 11, wherein two doses of a unit dosage form comprising from 1.5 to 5 mg of 2-bromolysergic acid diethylamide, or a pharmaceutically acceptable salt thereof, are administered to said subject over a period of 2 to 7 days.

13. The method of claim 12, wherein three doses of a unit dosage form comprising from 1.5 to 5 mg of 2-bromolysergic acid diethylamide, or a pharmaceutically acceptable salt thereof, are administered to said subject over a period of 4 to 20 days.

14. The method of claim 13, wherein three doses of a unit dosage form comprising from 1.5 to 3 mg of 2-bromolysergic acid diethylamide, or a pharmaceutically acceptable salt thereof, are administered to said subject over a period of 7 to 12 days.

15. The method of claim 14, wherein three doses of a unit dosage form comprising from 1.5 to 3 mg of 2-bromolysergic acid diethylamide, or a pharmaceutically acceptable salt thereof, are administered to said subject once every five days over a period of 11 days.

16. The method of any one of claims 1-4, wherein said 2-bromolysergic acid diethylamide, or a pharmaceutically acceptable salt thereof, is administered orally, subcutaneously, intravenously, or intramuscularly.

17. The method of claim 1, wherein said recurrent cluster headache disorder is refractory to treatment using corticosteroids, tricyclic antidepressants, calcium channel blockers, beta blockers, anticonvulsants, methysergide, or lithium.

18. The method of claim 2, wherein said chronic cluster headache disorder is refractory to treatment using corticosteroids, tricyclic antidepressants, calcium channel blockers, beta blockers, anticonvulsants, methysergide, or lithium.

19. The method of claim 3, wherein said episodic cluster headache disorder is refractory to treatment using corticosteroids, tricyclic antidepressants, calcium channel blockers, beta blockers, anticonvulsants, methysergide, or lithium.

20. The method of claim 4, wherein said cluster headache disorder is refractory to treatment using corticosteroids, tricyclic antidepressants, calcium channel blockers, beta blockers, anticonvulsants, methysergide, or lithium.

* * * * *

UNITED STATES PATENT AND TRADEMARK OFFICE
CERTIFICATE OF CORRECTION

PATENT NO. : 8,415,371 B2
APPLICATION NO. : 12/935737
DATED : April 9, 2013
INVENTOR(S) : John H. Halpern et al.

It is certified that error appears in the above-identified patent and that said Letters Patent is hereby corrected as shown below:

In the Claims:

Column 11, Claim 1, Line 23, replace "more, prophylactic" with --more prophylactic--.

Signed and Sealed this
Twenty-seventh Day of August, 2013

Teresa Stanek Rea
*Acting Director of the United States Patent and Trademark Office*